United States Patent [19]
Holcomb

[11] Patent Number: 5,607,667
[45] Date of Patent: Mar. 4, 1997

[54] BODY CARE COMPOSITIONS, METHOD OF USING SAME, AND METHOD OF GENERATING A RELATIVELY STABLE AQUEOUS SUSPENSION OF COLLOIDAL SILICA FOR USE THEREIN

[75] Inventor: Robert R. Holcomb, Hackleburg, Ala.

[73] Assignee: NovaTech, Inc., Nashville, Tenn.

[21] Appl. No.: 76,349

[22] Filed: Jun. 11, 1993

[51] Int. Cl.$^6$ .............................. A61K 9/14; A61K 33/00
[52] U.S. Cl. ...................... 424/70.1; 424/70.2; 424/724
[58] Field of Search .................................. 424/70, 62, 72, 424/401, 482

[56] References Cited

U.S. PATENT DOCUMENTS

| | | | |
|---|---|---|---|
| 4,000,317 | 12/1976 | Menda et al. | 424/69 |
| 4,089,997 | 5/1978 | Van Paesschen et al. | 427/171 |
| 4,978,437 | 12/1990 | Wirz | 204/192.23 |
| 5,286,478 | 2/1994 | Persello | 424/49 |
| 5,298,792 | 3/1994 | Manning | 257/758 |

OTHER PUBLICATIONS

Bleier "Colloids", Encyclopedia of Chemical Technology, fourth ed., vol. 6, John Wiley 1993 (month unavailable) pp. 812–840.

*Primary Examiner*—Jeffrey C. Mullis
*Attorney, Agent, or Firm*—Mallinckrodt & Mallinckrodt

[57] ABSTRACT

The effectiveness and/or hydrating ability of body care compositions, such as moisturizers, skin creams, body lotions, shampoo, hair conditioner, styling gel, styling mist, hair dye, bath additives, pedicure and manicure products, facial cleanser, facial mist, suntan lotions, and sunscreen lotions, are enhanced by the addition thereto of an aqueous suspension containing small concentrations of colloidal silica. The colloidal silica particles are charged and of a size between about 10 angstroms and 100 angstroms. An aqueous solution of colloidal silica particles is prepared by circulating the solution through a magnetic field so that the particles cut the field flux lines and build up a net negative charge thereon. It is preferred that the solution be passed through a magnetic void after passing through a magnetic field to allow the particles to configure themselves without the influence of external magnetic fields.

21 Claims, 3 Drawing Sheets

BODY CARE COMPOSITIONS, METHOD OF USING SAME, AND METHOD OF GENERATING A RELATIVELY STABLE AQUEOUS SUSPENSION OF COLLOIDAL SILICA FOR USE THEREIN

BACKGROUND OF THE INVENTION

1. Field

The present invention relates to body care compositions of matter such as moisturizers, lotions, creams, shampoos, hair conditioning and coloring agents, and to body care methods utilizing such compositions.

2. State of the Art

Many skin and hair care products on the market today make claims to rejuvenate skin and hair. Skin care products are claimed to contain moisturizers for dehydrated aging skin. Hair care products are claimed to build body into limp hair. Apparently none of these preparations address the central issue, which is the ongoing damage to the skin and hair from chronic dehydration.

Most skin care products have an oil or cream base. The problem to be overcome is not one of loss of skin oil but, rather, the chronic loss of moisture, which is one of the aging factors. There is a need for a product which will enable water to penetrate the dehydrated epidermal structures, i.e., skin, hair, and nails.

SUMMARY OF THE INVENTION

I have discovered that an aqueous composition containing small quantities of an inorganic colloidal silica (preferably specially processed to provide a stable, active configuration) greatly enhances the penetration of water, oils, and collagen into the epidermis of aging dehydrated skin. It also enhances the penetration of water, oils, and collagen into hair shafts. With enhanced penetration into the hair, hair coloring material penetrates the hair shafts to provide brighter color and longer retention of the color in the hair.

The inorganic colloidal silica can be beneficially used in a wide variety of body care compositions such as in shampoos, conditioners, styling gels, styling mists, hair coloring preparations, body lotions, face creams, skin creams, bath additives, pedicure and manicure applications, hand lotions, lip balms, lipsticks, suntan lotions, and sunscreen lotions. The use of the inorganic colloidal silica in facial cleansers, moisturizing creams, and facial mists provide a package for improvement of skin moisture, tone, and youthful appearance.

The active component of the invention comprises an aqueous suspension of a colloidal silica particles, preferably an aqueous solution with silica suspended therein. The silica particles are preferably from about 10 to about 100 angstroms in size and have an electrical charge thereon. The solution is preferably mixed in such a way that the colloidal particles become electrically charged, preferably by circulation of the solution through a magnetic field, and further, that the solution pass through a magnetic void during mixing so that the charged particles assume a stable configuration. The charge on the colloidal particles is stabilized to remain during a relatively long shelf life of the final product by the mixing process and by the addition of molar amounts of citrate or citrate salts. The invention comprises a hydration-enhancing composition of matter containing a unique blend of an inorganic colloidal silica in combination with a usual body care composition. The final body care compositions of the invention preferably contain colloidal silica in a concentration from about 1 part per million [ppm] to about 50 parts per million [ppm]. However, greater concentrations of colloidal silica are also equally effective, and lesser concentrations may be effective in many applications.

BRIEF DESCRIPTION OF THE DRAWINGS

The best mode presently contemplated for carrying out the invention in actual practice is illustrated in the accompanying drawings, in which.

DETAILED DESCRIPTION OF THE ILLUSTRATED EMBODIMENT

Enhanced body care compositions can be formulated by adding an aqueous suspension of colloidal silica to an existing body care composition such as a skin cream, body lotion, shampoo, hair conditioner, cleanser, etc. to bring the concentration of colloidal silica within the body care composition to a preferred range of from about 1 ppm to about 50 ppm. The body care product is then used in a normal manner, but it has been found that such product is more effective than the product without the colloidal silica added thereto. The presence of the colloidal silica in the product appears to dramatically increase the ability of the product to penetrate into body parts. Thus, the product and the water, oils, and collagen therein, if present, will actually penetrate into the epidermis, into the hair, or into the nails of a user so that the product can replace components lost from those body parts and moisturize such body parts. The result with skin care products is substantially more hydration or moisturization of the skin to keep its natural tone and consistency and reduce wrinkling, with hair care products to decrease drying and maintain body and managability, with hair coloring products to provide deeper and more lasting color since the coloring better penetrates the hair itself, and with the nails, better moisturization to provide better flexibility and strength. When using skin care products of the invention it is believed that the presence of colloidal silica allows the oil and collagen in the product to penetrate the superficial layers of the epidermus rather than merely sit on the surface of the epidermis, and allows the water in the product to penetrate more deeply into the deeper layers of the epidermis.

Figure 1:
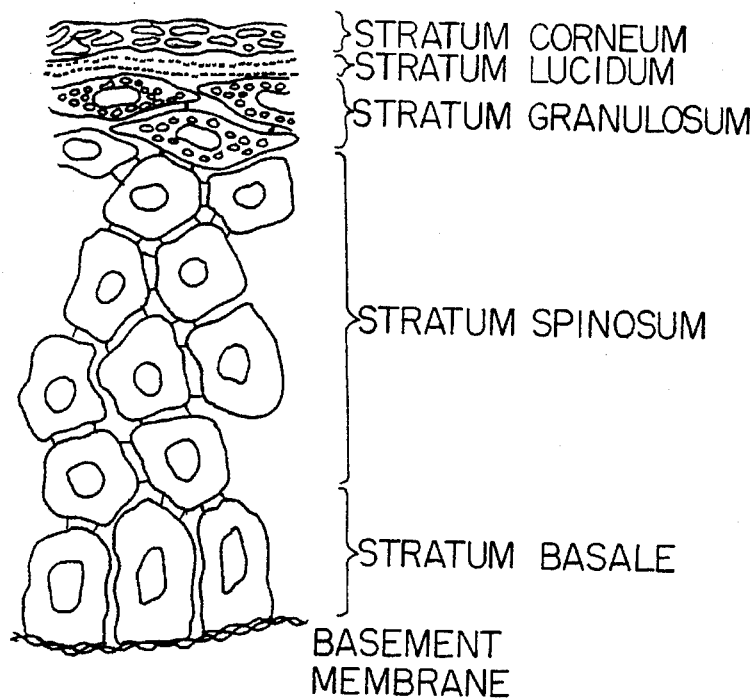
FIG. 1 is a representation of the structure of the human epidermis or skin.

FIG. 1 is a representation of the structure of the skin. The stratum corneum and stratum lucidum form the outer or superficial layers of the skin. It is believed that the presence of the colloidal silica particles of the invention in an oil or collagen containing composition aid in allowing the oils and collagen to penetrate the superficial layers of the skin. Thus, the oils and collagen will better penetrate the stratum corneum and stratum lucidum. The oils and/or collagen in the superficial layers of the skin will tend to hold moisture in the skin and retard the drying of the skin. It is further believed that the presence of the colloidal silica particles of the invention in a water-containing composition aid in allowing the water to penetrate deeply into the skin, probably all the way to the stratum basale and basement membrane. Such penetration of water into the skin moisturizes or hydrates the skin to combat skin drying by replacing water otherwise lost from the skin.

The aqueous suspension of colloidal silica preferably takes the form of a solution to be added in small amounts to body care compositions and is preferably prepared in such a way that the colloidal particles become charged (it is believed that the particles take on a net negative charge) and assume an active configuration and the charge and configuration is stabilized so that the particles remain charged and remain in suspension during a relatively long shelf life of the solution and a relatively long shelf life of any products made using the solution. The particles and solution may be stabilized by adding citric acid (tripotassium salt) to the solution containing the particles and pH adjusted with acetic acid so it will also contain traces of citrate and acetate. In a preferred form of the invention, the solution contains about 500 PPM colloidal silica, 0.001 moles/liter of potassium citrate, and traces of acetate, in purified distilled water. This aqueous solution may be added in very small amounts to body care compositions to aid penetration of moisture or oils into epidermal structures such as skin, hair, and nails.

To prepare the inventive composition, an aqueous solution of colloidal silica is first made up. This can be done by starting with a solution that is about 27% silicon dioxide in about 3 to about 4 molar NaOH. As one option, it has been found that citric acid or citric acid salts added in molar amounts about equal to the molarity of the NaOH improve the stability of the end solution. The starting solution and citric acid or citric acid salts, if present, is diluted very slowly, with stirring. Preferably, this is done over a period of several hours. Next, the solution is very slowly titrated with about 0.5–1.0 molar of an acid, usually hydrochloric or acetic acid, to a pH of between about 7.6 and 8.2. Again, this is preferably done over a period of several hours with constant stirring. The final concentration is a solution of preferably about 0.050% (about 500 parts per million) colloidal silica. At this time the silica is present as colloidal particles of between about 10 to 100 angstroms in size.

The nature of the silicate solution is represented by the following equations at 25° C.:

$$SiO_2 + 2H_2O \rightleftharpoons Si(OH)_4 \qquad (1)$$

$$Si(OH)_4 + OH^- \rightleftharpoons HSiO_3^- + 2H_2O \qquad (2)$$

$$2HSiO_3^- \rightleftharpoons Si_2O_3^- + 2H_2O \qquad (3)$$

$$HSiO_3^- + OH^- \rightleftharpoons SiO_3^= + H_2O \qquad (4)$$

Figure 2:
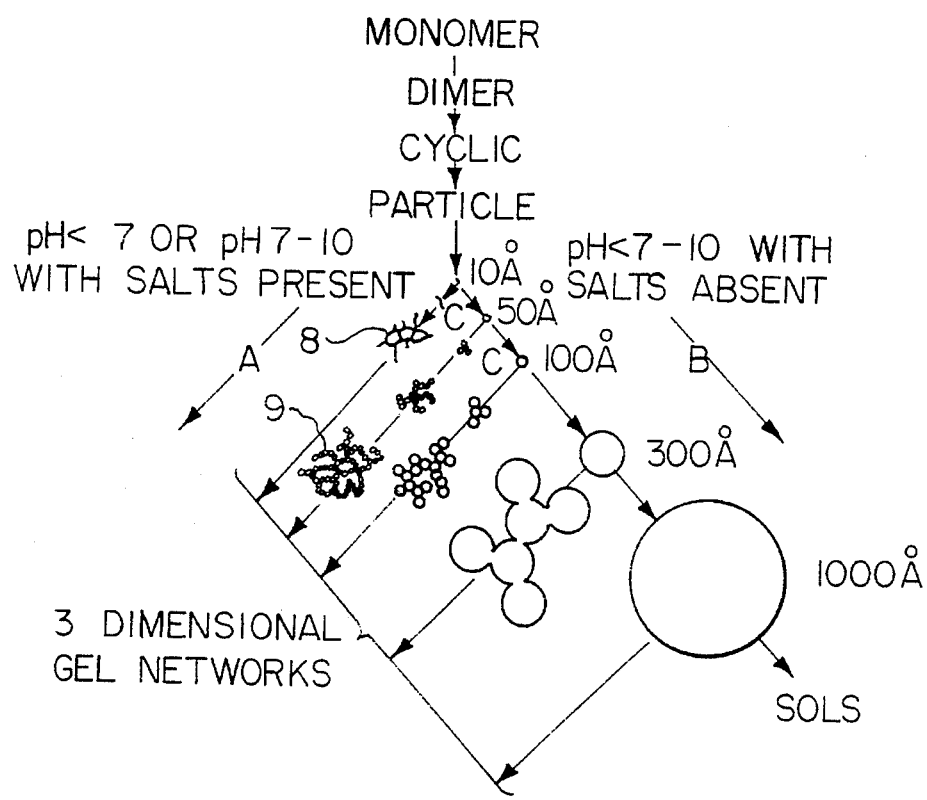
FIG. 2, a schematic representation of the believed polymerization behavior of silica.

FIG. 2 is a diagram from The Chemistry of Silica: Solubility, Polymerization, Colloid and Surface Properties, and Biochemistry, by Ralph K. Iler, published 1979 by Wiley, representing schematically the believed polymerization behavior of silica. Under normal circumstances, in a basic solution, shown by arrow B, silica particles in sol grow in size with decrease in numbers. In an acid solution or in the presence of flocculating salts, shown by arrow A, silica particles aggregate into three-dimensional networks and form gels. Neither the enlarged sols nor the silica gels are satisfactory for the invention. Thus, the growth of the sols or the formation of a gel has to be inhibited. In the preferred process for making the silica solution of the invention, as the pH is lowered, polymerization of monomer occurs to form particles, i.e., Si(OH)$_4$ condenses to form colloidal particles. The condensation forms Si—O—Si links. This is believed to lead to a highly porous, tangled network of branching chains as shown by reference numbers 8 and 9 in FIG. 2. These structures appear to accept electrical charge. These particles grow with the lowering of the pH as indicated by arrow A. The solution is inhibited from becoming a gel by the addition of citrate and by generating like charges on the particles which cause the particles to repel one another. Thus, the growth of the particles is stopped after the particles have grown to a size of between about 10 angstroms and 100 angstroms and with structures as shown at 8 and 9.

In order to generate a charge on the silica particles, it is preferred that during the mixing of the colloidal silica solution the solution be circulated through a magnetic field so that movement of the silica particles through the magnetic field generates the electrical charge on the silica particles. Such silica particles are believed to be a semi-conductor material. If the silica particles are passed through a magnetic field so as to cut through the lines of flux of the field, an electrical charge is generated on the particles as they cut through the lines of flux. The particles act as both a conductor and a capacitor, i.e., they generate a charge and store the charge. After passing through a magnetic field to generate a charge on the silica particles, it is preferred that the particles be passed through a space substantially void of any magnetic fields. This space allows each of the charged particles to then assume a configuration based on the charges on the particle and the internal bonding of the particle without regard to external fields. It is believed that this may provide a result similar to producing the particle in outer space and provides formation of a very stable colloidal particle. Circulation through the magnetic field and the magnetic void preferably takes place on a repetitive basis during generation of the colloidal solution. It has been found that with circulation through a magnetic field, the silica particles take on a net negative electrical charge.

Figure 3:
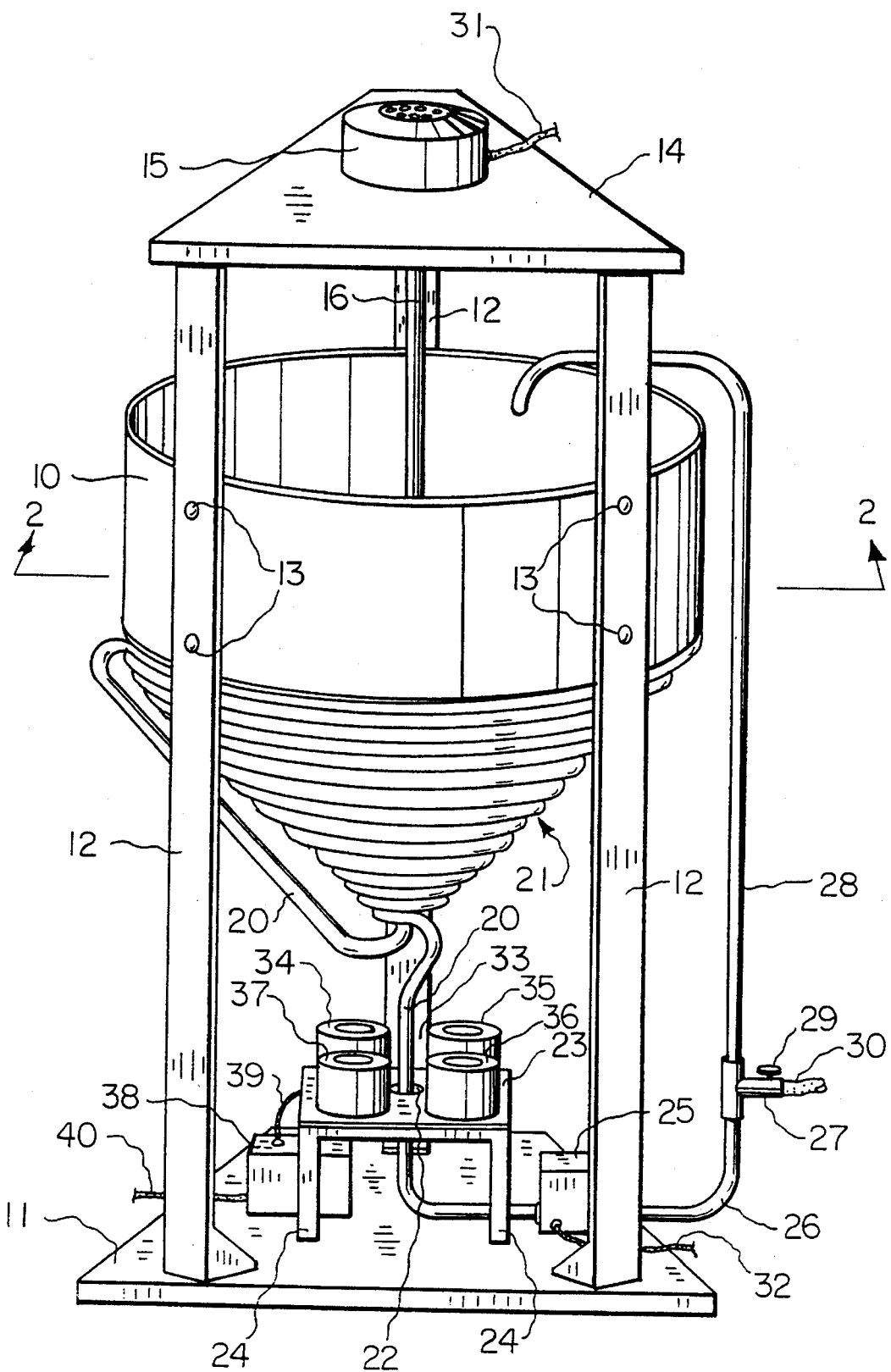
FIG. 3 is a perspective view of a mixing apparatus useful for making colloidal silica solutions according to the invention.
Figure 4:
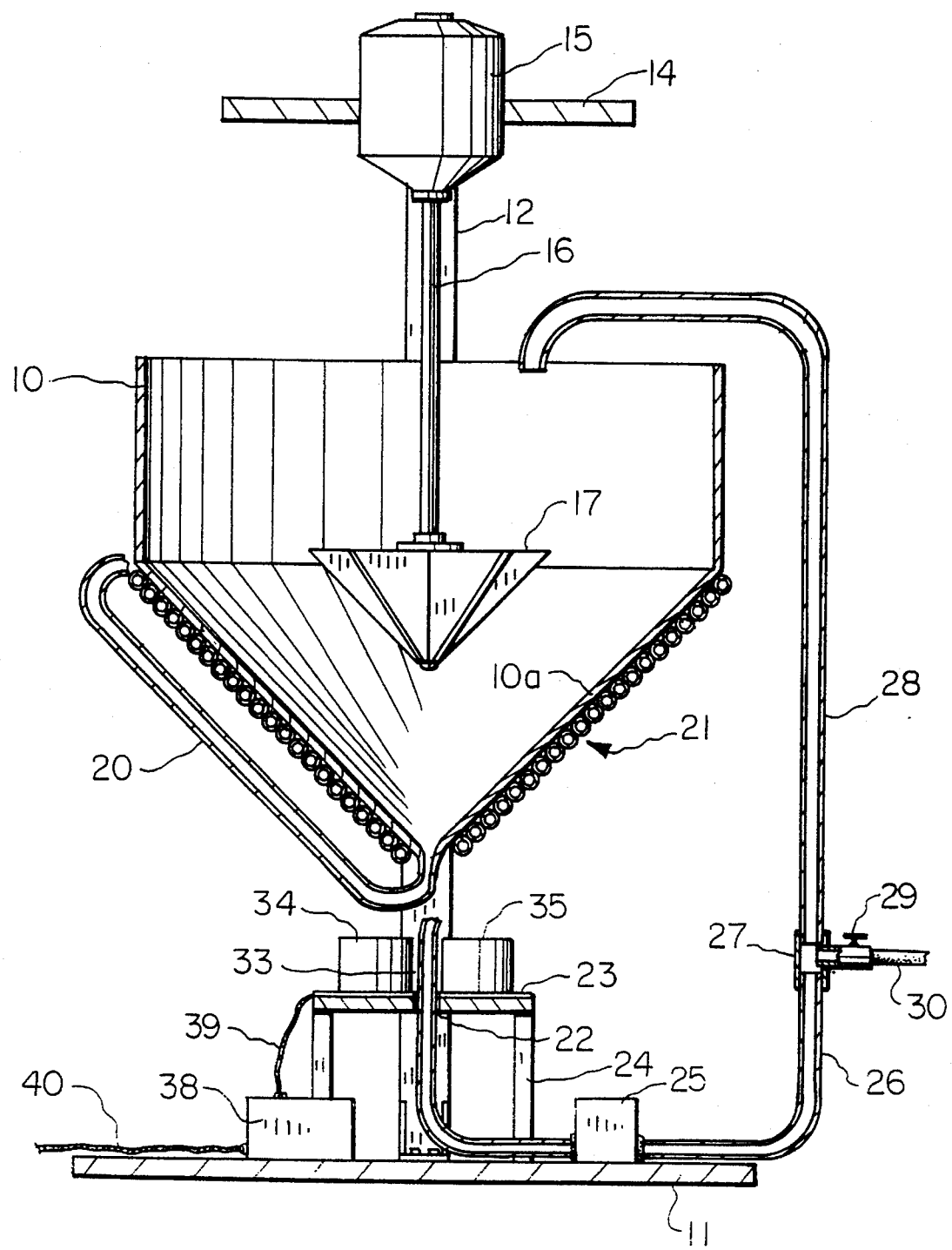
FIG. 4, a vertical section taken on the line 2—2 through the center of the mixing apparatus of FIG. 1, but with some parts shown in elevation.

Apparatus which has been found advantageous for mixing the colloidal solution is shown in FIGS. 3 and 4. As shown, a mixing chamber 10 is supported above base 11 by supporting legs 12, secured to mixing chamber 10 as by screws 13. A platform 14 is mounted to the tops of legs 12 and extends over mixing chamber 10 to support a motor 15. A shaft 16 extends from motor 15 to support a mixing blade 17, FIG. 4, in mixing chamber 10. The lower portion 10a of mixing chamber 10 is of conical formation. The mixing chamber and the supporting legs are preferably made of a nonferrous material.

Nonferrous tubing 20 extends from the vortex of the lower conical portion 10a of mixing chamber 10 to the top of the conical portion where it is wrapped into a helical coil, indicated generally as 21, around the conical portion 10a of mixing chamber 10. From the bottom of helical coil 21, tubing 20 extends through an opening 22 in platform 23 supported above base 11 and below mixing chamber 10 by legs 24, and to pump 25. From pump 25, tubing 26 extends to a tee fitting 27, and tubing 28 continues from the tee fitting to the top of mixing chamber 10. A valve 29 is positioned in the base of tee 27 and controls flow into tubing 30 extending from the base of tee 27. Motor 15 and pump 25 are both electrically powered so have electrical wires 31 and 32, respectively, extending therefrom.

Four electromagnets 34, 35, 36, and 37 are securely mounted in platform 23 such as by being received in recesses therein as shown by broken lines in FIG. 4. Magnets 34, 35, 36, and 37 are arranged so that the poles of the magnets are in a single plane and form the vertices of a quadrilateral shape in that plane. Preferably that quadrilateral shape is a square as for the arrangement illustrated. The poles of adjacent magnets are of opposite orientation such as indicated by the "+" and "−" signs in FIG. 3. With this arrangement, the two positive poles, shown as magnets 34 and 36, form one pair of opposite vertices of the quadrilateral shape while the two negative poles, shown as magnets 35 and 37, form the other pair of opposite vertices. Each of the magnetic poles is magnetically attracted by the two oppositely charged, adjacent poles and repelled by the opposite like charged pole. The four magnets exert a sphere of magnetic influence on one another and create a magnetic field which extends above the magnets, i.e., mostly above the plane containing the poles of the magnets, to encompass the helical coil 21. This provides the magnetic field through which the solution flows during mixing. As the colloidal particles flow through the helical coil 21, they cut through the lines of magnetic flux of the magnetic field. This produces the net negative electrical charge on the particles. It has been found that at least a portion of the space 33 immediately between the magnets is an area substantially void of magnetic field. Thus, a magnetic field is created above the magnets and below the magnets (the field below the magnets is contained by platform 23 if the platform is made of magnetic material such as stainless steel), but the area immediately between the magnets is substantially shielded from all magnetic fields, including, it is believed, the earth's magnetic field. Tubing 20 passes through the area of magentic void between the magnets prior to passing through opening 22 in platform 23 and is oriented parallel to each of the four electromagnets and is preferably spaced equidistant from each. As the particles circulate through the helical coil 21, a charge is generated on the particles. When the charged particles pass through the area of magnetic void, the outside magnetic forces on the particles are removed and the particles configure themselves based on the charges thereon and the internal particle bonds to achieve a relatively stable configuration. This configuration remains as the particles emerge from the magnetic void, even when the particles pass through a further magnetic field below the magnets. The presence of the citrates appears to further stabilize the particles.

It is preferred that the four electromagnets 34, 35, 36, and 37 be identical, except for their pole orientation, and that they each produce approximately equal magnetic flux. Electromagnets which create about 2000 to 3000 gauss each have been found satisfactory, and in such instances, each magnet should produce equal flux within plus or minus 200 gauss, i.e. the gauss produced by such magnets should all be equal within a range of about 400 gauss. Also, the magnetic flux for each magnet should be centered in each pole. The electromagnets are powered by a D.C. power supply 38 with wires 39 connecting the power supply to the magnets in standard fashion. A wire 40 extends from D.C. power supply 38 to a source of electrical power, such as a source of standard 120 volt AC power, not shown. It may be necessary to cool the electromagnets. Such cooling may be accomplished in normal manner by circulating a cooling fluid, such as cold water, through a cooling jacket, not shown, surrounding the electromagnets or surrounding the heads of the electromagnets. Also, while electromagnets are shown and currently preferred, permanent magnets may be used. In order to obtain the desired high magnetic field for large mixing equipment, exotic permanent magnets such as neodemium magnets would preferably be used.

To prepare the colloidal suspension of the invention using the apparatus shown and described, mixing chamber 10 is filled with purified water. The use of purified water is presently preferred since it is believed that the water penetrates deeply into the epidermis. The water is purified by series filtering through various filter beds depending upon the impurities in the starting water, by then heat distilling the water, aerating it, and then passing it through an ultraviolet light chamber. It has been found that for most public water supplies, the water should be first chlorinated to 3 PPM and aerated, then passed through a $CaMgCO_3$ (crushed marble) filter, a +35−20 mesh clinoptilolite filter, a particulate filter, and a −20+35 mesh activated carbon filter, before aeration and ultraviolet sterilization.

The purified water is circulated by pump 25 from mixing chamber 10, through the helical coil 21 and the magnetic field generated by electromagnets 34, 35, 36 and 37, through the magnetic void between the magnets, and back into mixing chamber 10 on a continuous basis for about 30 minutes. A silica concentrate comprising 27% silicon dioxide in 3 molar NaOH is then added to the circulating purified water. This mixture is circulated through the helix and magnetic field for about four hours. During this four hours of circulation, equal molar concentrations of citric acid in the form of tripotassium salt is slowly added to the solution. After circulation for about four hours with the slow addition of tripotassium salt, the pH of the solution is adjusted to pH 7.68 with acetic acid (1 molar). The adjusted solution is then circulated for an additional two hours. The resulting solution is then diluted with purified water to a final desired concentration for addition to the body care products, usually to a concentration of 50 PPM or greater, preferably to a concentration of about 500 PPM. Circulation through the helix and the magnetic void is continuous during the whole procedure. When finished, the silica solution is removed from the apparatus by opening valve 29 in tee 27 to allow the finished solution to flow through tubing 30 to storage, packaging, or the next stage of mixing.

It is preferred that the helical coil 21 be oriented so that the mixture travels during circulation therethrough in the direction it would normally circulate when draining from a basin, that is, counterclockwise in the northern hemisphere and clockwise in the southern hemisphere.

The following examples show how the aqueous suspension of colloidal silica can be used to enhance otherwise ordinary body care compositions.

EXAMPLE I

One cc of a colloidal silica solution of the invention with a silica concentration of 500 PPM was added to 100 ccs of Vasoline Intensive Care Lotion®. After the addition of the silica solution, it was noted that the lotion showed increased absorption into the skin, estimated as a ten-fold increase in absorption, and was more effective in moisturizing the skin.

EXAMPLE II

One cc of a colloidal silica solution of the invention with a silica concentration of 500 PPM was added to 100 cc of Prell® shampoo. Hair washed with the shampoo with the colloidal silica resulted in hair having a fuller and softer feeling and more manageable than hair washed in the shampoo without the colloidal silica. The shampoo itself was more viscous with the silica solution added and produced thicker lather during use.

EXAMPLE III

A cleansing primer can be used to remove skin oils and/or make-up prior to the application of a hydrating mist. A preferred cleansing primer contains the following body care components listed as percentages by weight:

43.906% water, 50.00% of an aqueous suspension of the invention containing 50 ppm colloidal silica, 5.00% ammonium laureth sulfate and decyl polyglucose, 0.25% hydrolyzed collagen, 0.025% tetrasodium EDTA, 0.444% hydroxyprofyl cellulose, 0.25% panthanol, 0.025% fragrance, 0.10% sodium hydroxymethyl glycinate.

By using the cleansing primer of the invention, the face feels cleaner than when using other face cleaners or soaps and feels cooler and smoother.

EXAMPLE IV

A hydrating misting agent comprises an aqueous suspension of the invention of colloidal silica in a preferred concentration range of about 50 ppm, optionally, collagen in a concentration of about 43 ppm, and 0.25% sodium hydroxymethyl glycinate. Such a hydrating mist is used by spraying it on the face and neck. A mask of facial tissue or thin collagen fibers may then be applied along with additional hydrating mist to keep it very moist for about twenty minutes. The water from the mist penetrates the skin, i.e., the epidermal cells and interstitial spaces, and the face feels firmer and the tiny surface lines diminish. As compared to other facial masks, use of the misting agent and facial mask of the invention results in a reduction of wrinkles and a face with a more youthful glow and feel.

EXAMPLE V

A body care composition, in this instance a surface active cream, contains the following body care components (all percentages are by weight): 58.39% water, 12.81% isopropyl myrestate, 8.44% mineral oil, 4.00% glycerine, 3.84% sorbitan stearate, 2.00% cocoa butter, 1.43% beeswax, 1.20% stearic acid, 1.20% cetyl alcohol, 1.12% polysorbate 60, 1.00% aloe vera oil, 0.99% glyceryl stearate S.E., 1.00% dimethicone, 0.75% triethanolamine, 0.30% sodium borate, 0.25% panthanol, 0.15% fragrance, 0.15% propylparaben, 0.15% methylparaben, 0.83% of an aqueous suspension of the invention of 500 ppm colloidal silica, and 0.25% sodium hydroxymethyl glycinate. The colloidal silica is present in a final concentration of about 4.15 parts per million [ppm]. Use of the surface active cream of the invention results in a smoother and softer feeling skin that maintains that feeling and look longer than with use of prior art creams and lotions and, importantly, the cream of the invention does not leave the oily and greasy feeling of the prior art creams and lotions.

Whereas this invention is here described with reference to embodiments thereof presently contemplated as the best mode of carrying out such invention in actual practice, it is to be understood that various changes may be made in adapting the invention to different embodiments without departing from the broader inventive concepts disclosed herein and comprehended by the claims that follow.

I claim:

1. A body care composition for application to a body part for hydrating the body part, comprising one or more body care components; and an aqueous suspension of colloidal silica particles, wherein the aqueous suspension is generated by lowering the pH of an alkaline silica solution during circulation of the solution through a magnetic field greater than the earth's magnetic field to form charged colloidal silica particles in the solution.

2. A body care composition according to claim 1, wherein the body part is an epidermal structure of the body and the body care component absorbed hydrates the epidermal structure.

3. A body care composition according to claim 2, wherein the body care component absorbed is water.

4. A body care composition according to claim 1, wherein the aqueous suspension has been circulated through the magnetic field in a helical coil.

5. A body care composition according to claim 1, wherein the particles of colloidal silica are from about 10 to about 100 angstroms in size.

6. A body care composition according to claim 2, wherein the colloidal silica particles are present in concentration of from about 1 part per million to about 50 parts per million.

7. A body care composition according to claim 1, wherein the one or more body care components is a body care component selected from the group consisting of shampoo, conditioner, styling gel, styling mist, body lotion, skin cream, face cream, bath additive, pedicure composition, manicure composition, hand lotion, lip balm, lipstick, suntan lotion, sunscreen lotion, and skin cleansing composition.

8. A body care composition according to claim 1, wherein the aqueous suspension of colloidal silica has been circulated through an area substantially devoid of magnetic fields after having been circulated through the magnetic field.

9. A body care composition according to claim 8, wherein the aqueous suspension of colloidal silica contains silica particles of size between about 10 Angstroms and about 100 Angstroms.

10. A body care composition according to claim 7, wherein the aqueous suspension of colloidal silica has been generated by continuously circulating a solution of silica in about three to about 4 molar NaOH through the magnetic field and magnetic void over a period of time during which time the solution has been diluted with water to a concentration of about 0.050% silica and the solution has been titrated with an acid to a pH of between about 7.6 and 8.2.

11. A body care composition for application to a body part for hydrating the body part, comprising one or more body care components; and an aqueous suspension of colloidal silica particles, wherein the aqueous suspension is generated by combining over a period of time a solution of silica in about 3 to about 4 malor NaOH with water to a final concentration of the combination of about 0.05% silica while continuously circulating the combination through a magnetic field greater than the earth's magnetic field and titrating the combination with an acid to a pH of between about 7.6 and 8.2.

12. A body care composition according to claim 11, wherein the particles of colloidal silica are from about 10 to about 100 angstroms in size.

13. A body care composition according to claim 11, wherein the period of time over which the solution of silica is combined with the water is a period of several hours.

14. A body care composition according to claim 11, wherein the titration of the combination of solution of silica and water takes place over a period of several hours.

15. A body care composition for application to a body part for hydrating the body part, comprising one or more body care components; and an aqueous suspension of colloidal silica particles, wherein the aqueous suspension is generated by combining over a period of time during which period of time the combination is circulated through a magnetic field greater than the earth's magnetic field, water and a solution of silica to form a resulting aqueous suspension of colloidal silica particles.

16. A body care composition according to claim 15, wherein the particles of colloidal silica are from about 10 to about 100 angstroms in size.

17. A body care composition according to claim 15, wherein the aqueous suspension of colloidal silica particles prior to its combination with the one or more body care components has a pH of between about 7.6 and about 8.2.

18. A body care composition according to claim 15, wherein the aqueous suspension of colloidal silica particles prior to its combination with the one or more body care components has a concentration of colloidal silica particles of about 0.050%.

19. A body care composition according to claim 15, additionally including citrate.

20. A body care composition according to claim 19, wherein the citrate is present in the aqueous suspension that is combined with the one or more body care components in a concentration of about 0.001 moles/liter.

21. A body care composition according to claim 15, additionally including acetate.

* * * * *